United States Patent
Hawkins et al.

Patent Number: 5,304,370
Date of Patent: Apr. 19, 1994

[54] HAIR RELAXER COMPOSITION AND ASSOCIATED METHODS

[75] Inventors: Geoffrey R. Hawkins, Jacksonville; Clyde B. Simpson, Jr., Jacksonville Beach, both of Fla.; Gustave J. Klein, Great Neck, N.Y.

[73] Assignee: Revlon Consumer Products Corporation

[21] Appl. No.: 895,951

[22] Filed: Jun. 9, 1992

[51] Int. Cl.$^5$ .............................. A61K 7/09; A61K 7/06
[52] U.S. Cl. .................................. 424/71; 132/205
[58] Field of Search .................. 424/71, 72, 450; 132/202, 204; 524/801

[56] References Cited

U.S. PATENT DOCUMENTS

| | | | |
|---|---|---|---|
| 4,524,175 | 6/1985 | Stanley, Jr. | 524/801 |
| 4,947,878 | 8/1990 | Crews . | |
| 5,068,101 | 11/1991 | Akhtar et al. | 424/71 |
| 5,077,042 | 12/1991 | Darkwa . | |

OTHER PUBLICATIONS

Cosmetics & Toiletries, vol. 106, Jul. 1991, pp. 49–51.
Cosmetics & Toiletries, vol. 94, Apr. 1979, pp. 51–56.

Primary Examiner—Thurman K. Page
Assistant Examiner—Sally Gardner
Attorney, Agent, or Firm—Julie Blackburn

[57] ABSTRACT

A hair relaxer composition comprising a mixture of:
a) a base composition containing a water phase comprised of sodium hydroxide in water, and an oil phase, wherein the water phase is dispersed in the oil phase in the form of water in oil emulsion micelles,
b) an additive composition comprised of a water in oil emulsion whereby the mixture of (a) and (b) is an emulsion within an emulsion.

6 Claims, 3 Drawing Sheets

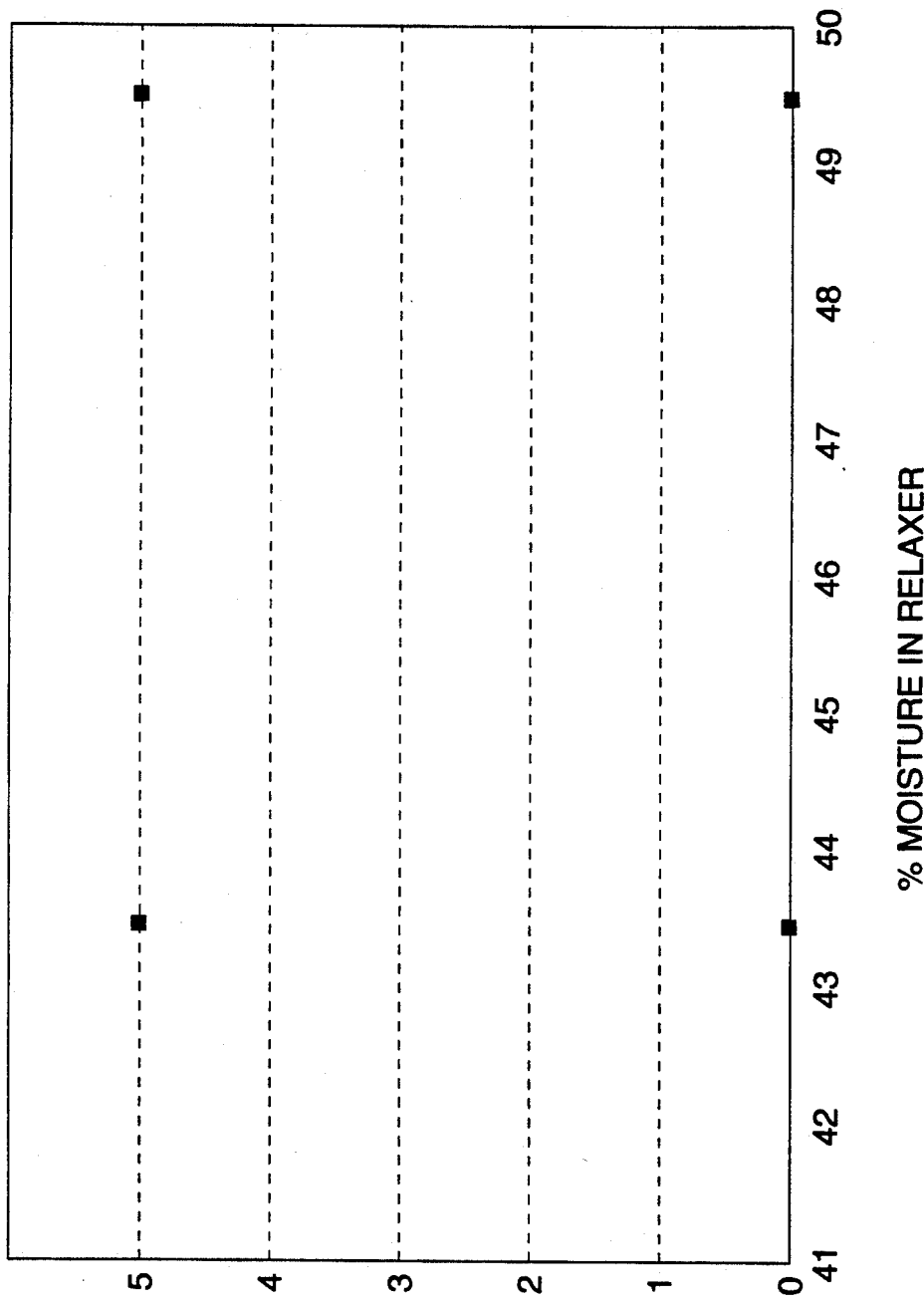

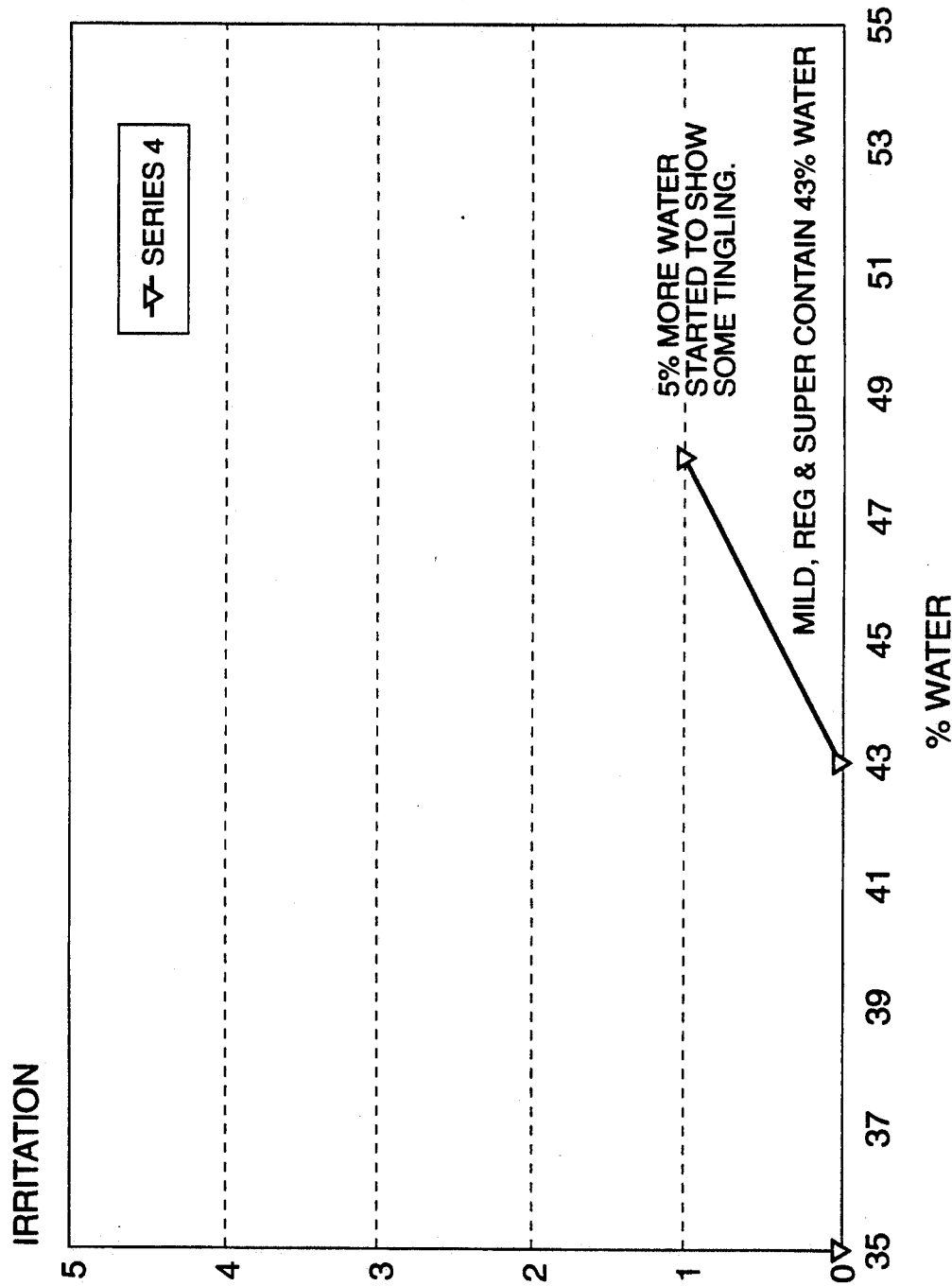

HAIR RELAXER COMPOSITION AND ASSOCIATED METHODS

TECHNICAL FIELD

The invention is in the field of hair relaxers or hair straighteners.

BACKGROUND OF THE INVENTION

Hair relaxers or straighteners are very popular today and widely used by individuals desiring to straighten very curly or kinky hair.

In man, the hair fiber consists of the cuticle, cortex, and medulla. The cuticle surrounds the actual fiber and consists of overlapping flat scale-like cells. The cuticle protects the hair fiber and is generally more resistant to penetration and attack by chemical agents. The cortex consists of spindle shaped cells which are oriented along the axis of the hair fiber. Microfibrils of the protein keratin are found in cortical cells. The medulla runs down the center of the hair fiber and usually consists of hollow cells.

Straightening or relaxing the hair fiber involves breaking the disulfide bonds found in the hair fiber proteins and reorienting them so that the hair fiber forms the desired "straight" configuration.

In the 1920's hair relaxers were generally soap based systems containing sodium hydroxide in conjunction with typical fatty acids such as stearic acid. These relaxers were often caused burning or stinging, thus a base of petrolatum was usually first applied to the hair.

In the 1950's it was discovered that if the relaxer composition was presented in a water in oil emulsion form, the results were improved and the burning and stinging was considerably reduced. In such systems, the sodium hydroxide was dissolved in water. The water mixture was then dispersed or emulsified into an oil mixture to create a water in oil emulsion. As the formulators increased the concentration of the lye containing water phase, they added more oil to the relaxer formulation so that the formula was approximately 50 percent water phase and 50 percent oil phase. It was discovered that a 50/50 mixture of oil and water phases was optimum. A relaxer formulation with higher concentrations of oil was more stable, but usually less effective in providing relaxing properties. On the other hand, a relaxer with increased amounts of water phase (and hence more effective as a relaxer) often was unstable, and caused burning and stinging upon application, particularly when the lye concentration became too high.

Then in the 1960's emulsion control was improved. It was discovered that relaxers were much improved when water phase was dispersed in the oil in a micelle configuration. The resulting relaxer formulation was still a water in oil emulsion containing about 50 percent water phase and about 50 percent oil phase, the difference being in the micellular configuration of the water/oil droplets. When the relaxer composition was applied to hair and massaged in, the micelle broke, released the water/lye mixture which then penetrated into the hair fiber cortex. The oil portion of the micelle rested on the cuticle and performed a conditioning effect. The result was a relaxer which was more stable, less painful to use, and much more commercially desireable.

Other systems evolved as formulators attempted to achieve the same relaxing effects but without the use of lye. A guanidine carbonate/calcium hydroxide system was developed and is still used today. In guanidine based systems, a water insoluble inorganic hydroxide such as calcium hydroxide is reacted with a water soluble guanidine salt such as guanidine carbonate. The guanidine hydroxide mixture is then applied to the hair and acts as an effective hair straightener, but quickly converts back to guanidine carbonate which has no hair straightening properties. Guanidine carbonate/calcium hydroxide systems are very popular and widely used today. They are somewhat milder than lye based systems, but are generally considered to be less effective in achieving straightening or relaxing effects.

Attempts to improve existing systems were complicated by the fact that the inventors were unable to determine any correlation between the following variables: the percentage of water in the formulation vs. the irritation level, the ability of the relaxer formulation to penetrate hair vs. the irritation level, and the active level of sodium hydroxide vs. the irritation level within the limits of acceptability.

In terms of straightening effectiveness, lye is still the ingredient of choice. Thus it is most desireable to use lye, yet to alleviate the other problems associated with its use.

Accordingly, one of the objects of the invention is to make a lye based relaxer formulation which exibits maximal effectiveness in relaxing or straightening hair, and minimizes the undesireable side effects which cause irritations such as burning or stinging.

Another object of the invention is to make a lye based relaxer system which exhibits improved shelf stability over the formulations currently marketed.

Another object of the invention is to make a lye based relaxer composition wherein the effectiveness of the composition in straightening hair, and the skin irritation caused by the composition can be predicted based upon the specific formulation of the composition.

SUMMARY OF THE INVENTION

The invention is directed to a hair relaxer composition comprising a mixture of:
a) a base composition containing a water phase comprised of sodium hydroxide in water, and an oil phase, wherein the water phase is dispersed in the oil phase in the form of water in oil emulsion micelles,
b) an additive composition selected from the group consisting of a water in oil emulsion and an anhydrous oil composition,
whereby the mixture of (a) and (b) is an emulsion within an emulsion.

The invention is also directed to a method for manufacturing a relaxer for human hair comprising the steps of:
a) mixing a base composition containing a water phase comprised of sodium hydroxide in water, and an oil phase, wherein the water phase is dispersed in the oil phase in the form of water in oil emulsion micelles, with
b) an additive composition selected from the group consisting of a water in oil emulsion and an anhydrous oil composition,
to yield a hair relaxer composition which is an emulsion within an emulsion.

The invention is also directed to a method for relaxing human hair comprising the steps of:

a) mixing a base composition containing a water phase comprised of sodium hydroxide in water, and an oil phase, wherein the water phase is dispersed in the oil phase in the form of water in oil emulsion micelles, with an additive composition selected from the group consisting of a water in oil emulsion and an anhydrous oil composition, to yield a hair relaxer composition, b) applying the hair relaxer composition to the hair for a period of time sufficient to relax the hair, c) conditioning the hair with a conditioning composition.

DESCRIPTION OF THE DRAWINGS

FIG. 2: Illustrates that there is no correlation between scalp irritation and water concentration in Revlon-Realistic's current commercial lye based relaxer, as further explained in Example 6.

FIG. 3: Illustrates a positive correlation between scalp irritation and water concentration in the relaxer composition of the invention, as further explained in Example 7.

DETAILED DESCRIPTION

Figure 1:
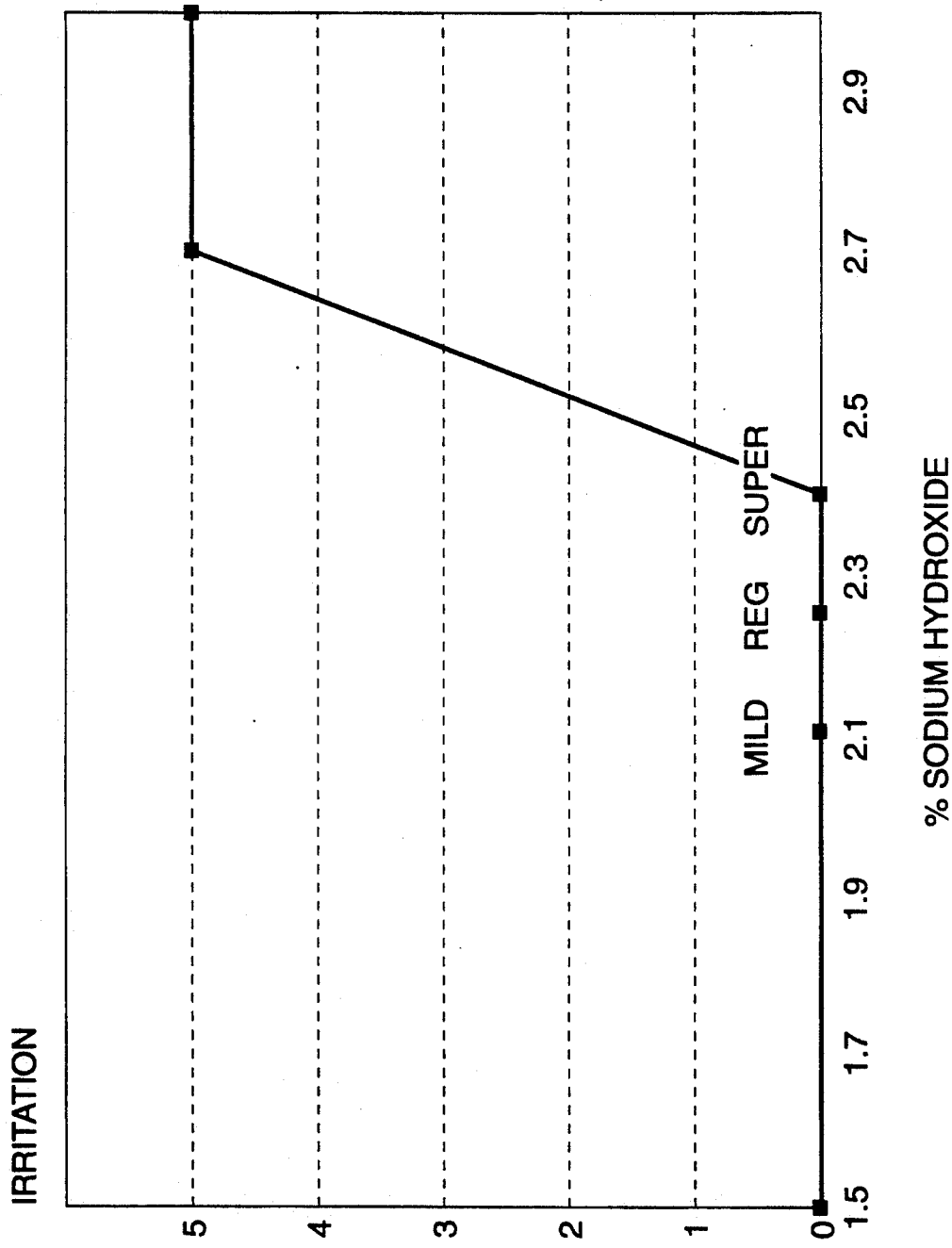
FIG. 1: Illustrates the correlation between sodium hydroxide concentration and scalp irritation in the relaxer compositions of the invention, as further explained in Example 5.

The term "hair relaxer" or "hair relaxer composition" means a composition, which, when applied to very curly or kinky hair is capable of breaking the disulfide bonds found in the hair fiber protein, so that these disulfide bonds are capable of reorientation to result in hair which is no longer kinky or curly, or has become straightened.

The hair relaxer composition of the invention comprises a mixture of two separate compositions, a base composition and an additive composition. The two compositions are mixed immediately prior to use.

The base composition comprises a water in oil emulsion wherein the water phase is dispersed in the oil phase in a micelle configuration as set forth in FIG. 1. The micelle orientation is achieved, most unexpectedly, through normal mixing processes. The base composition of the invention comprises about 40 percent by weight (about 37–43%) of the base composition of an oil phase and about 50–60 percent by weight of the base composition of a water phase. The oil phase comprises oils and waxes, as well as oil soluble additives such as emollients, quaternary polymers, humectants, preservatives, proteins, vitamins, thickeners, fragrances, surfactants, etc. Suitable oils and/or waxes include mineral oil, petrolatum, synthetic waxes, isoparaffin, paraffin, lanolin, squalene, propylene glycol, stearyl alcohol, oleyl alcohol, cetearyl alcohol, cetyl alcohol, laneth, polydimethylsiloxanes, cetearyl alcohol, or mixtures thereof. Suitable surfactants include Octoxynol 1-70, stearic acid, Polysorbate 20-100, PEG 2-150 stearate, Steareth 2-100, Laneth 5-75, PEG 1-100 lanolin, or mixtures thereof.

The term "Octoxynol 1-70" means an ethoxylated alkyl phenol of the formula $C_8H_{17}C_6H_4(OCH_2CH_2)_nOH$ wherein n has an average value of 1-70. The term "Polysorbate 20-100" means collectively Polysorbate 20, 21, 40, 60, 61, 65, 80. The term "PEG 2-150 stearate" means the polyethylene glycol ester of stearic acid having the formula: $CH_3(CH_2)_{16}C-(OCH_2CH_2)_nOH$ wherein n has the average value of 2-150. The term "Steareth 2-100" means the polyethylene glycol ether of stearyl alcohol having the formula $CH_3(CH_2)_{16}CH_2(OCH_2CH_2)_nOH$ where n has an average value of 2-100. The term "Laneth 5-75" means the polyethylene glycol ether of lanolin alcohol with an average ethoxylation value of 5-75. The term "PEG 1-100 lanolin" means the polyethylene glycol derivative of lanolin with an average of 1-100 moles of ethylene oxide.

The water phase of the base composition comprises a solution of water containing sodium hydroxide, generally about 40-60% by weight of the water phase of sodium hydroxide with about 40-45% being preferred. In addition, the water phase may contain other water soluble constituents such as color indicators, humectants, fragrances, preservatives, and so on.

In the preferred embodiment of the invention, the base composition contains, by percent weight of the total base composition, about 35-50 percent oil phase, about 35-50% water phase, and about 1-20% surfactants. The amount of sodium hydroxide which is dissolved in the water phase should be such that the sodium hydroxide concentration is about 1.5-3.5 percent by weight of the total base composition.

The additive composition may be either a water in oil emulsion or an anhydrous oil composition. In the preferred embodiment of the invention the additive composition comprises a water in oil emulsion comprising, by weight of the additive composition, about 0.1-70% water, about 30-90% oil, and about 0.01-35% surfactant. Suitable oils include mineral oil, lanolins, oleyl alcohol, wheat germ oil, linoleic acid, linolenic acid, polydimethylsiloxane, PEG-lanolins, or mixtures thereof. In addition to water, the water phase may contain other water soluble constituents such as preservatives, fragrances, colorants, humectants, emollients, and so on. Preferably the surfactant is a nonionic surfactant, most particularly a octylphenoxyethanol of the formula:

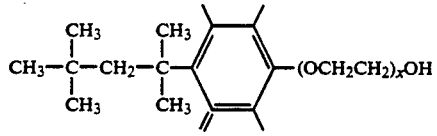

wherein x is 1-50.

The additive composition may also comprise an anhydrous oil composition containing various oils and surfactants in combination. Preferably the anhydrous oil composition comprises 1-60% by weight of the additive composition of surfactants and 1-90% by weight of the additive composition of oils, in addition to other desire addtivies such as fragrances.

It is important to note that when the additive composition is a water in oil emulsion, the emulsion within emulsion characteristics of the relaxer composition are easily achieved by mixing the additive composition. The emulsion within emulsion characteristics of the relaxer composition are easily achieved by mixing the additive and base immediately prior to use. On the other hand, if the additive composition is an anhydrous oil composition, the base composition will then be in an emulsion within an emulsion format which is modified in terms of water content upon addition of the anhydrous oil composition.

To obtain the hair relaxer composition of the invention, about 40 to 90 parts by weight of the total composition of base composition are mixed with about 10 to 60 parts by weight of the total composition of additive composition immediately prior to use. In the preferred embodiment, about 10 to 30 parts by weight of a water in oil emulsion additive composition are mixed with about 70 to 90 parts by weight of the base composition to yield a finished relaxer composition comprising 35–45% water, 55–65% oil and 1.5–3.5% sodium hydroxide. The composition is immediately applied to the hair and allowed to remain for 5–30 minutes. The hair is then treated with a conditioning agent, in particular the hair is shampooed with a shampoo having a pH range of approximately 3.5–6.0. The acidic nature of the shampoo acts to neutralize the sodium hydroxide which remains on the hair.

The hair relaxer of the invention exhibits surprising results over the prior art compositions. First, variables such as irritation of the relaxer vs. water content of the formulation, and irritation of the relaxer vs. sodium hydroxide concentration exhibited a positive correlation, whereas in the prior art relaxers tested, no correlation was found between the scalp irritation vs. water content and scalp irritation vs. sodium hydroxide content.

Furthermore, the relaxer formulation of the invention is more effective in relaxing or straightening the hair, yet is less prone to cause the burning and stinging often associated with the use of lye based relaxers.

Also, the micelle configuration of the base composition of the invention can be achieved by normal mixing procedures whereas the prior art base compositions must be mixed by milling to achieve a water in oil micelle configuration.

Finally, the preferred relaxer formulation of the invention contains more than 50 percent by weight of oils or hydrophobic material, and less than 50 percent by weight of water phase, yet it retains stability without sacrificing relaxer effectiveness. This finding is in direct contradition to the prior art relaxers wherein if the concentration of oil phase in these relaxers was more than about 50 percent, and the water content less than 50 percent, the relaxer began to lose effectiveness.

The invention is also directed to a method for relaxing human hair comprising the steps of:
a) mixing a base composition containing a water phase comprised of sodium hydroxide in water, and an oil phase, wherein the water phase is dispersed in the oil phase in the form of water in oil emulsion micelles, with
b) an additive composition selected from the group consisting of a water in oil emulsion and an anhydrous oil composition, to yield a hair relaxer composition which is an emulsion within an emulsion.

As mentioned previously, one factor which contributes to the effectiveness of the relaxer composition of the invention is the micelle configuration of the base composition and the emulsion within an emulsion characteristics achieved when the water in oil emulsion additive and base compositions are mixed together. While with prior art relaxer compositions, the micelle configuration can only be achieved with milling. In the relaxer base composition of the invention, the micelle configuration can be achieved by only normal mixing. In order to make the hair relaxer compositions of the invention, about 40–90 percent by weight of the total composition of base composition is mixed with 10–60 percent by weight of the total composition of additive composition using normal mixing procedures. The composition is then immediately applied to the hair. In the preferred embodiment of the invention, about 10–30 percent additive is mixed with 70–90 percent base composition, the formulations of the base and additive compositions being as discussed previously.

The invention is also directed to a method for relaxing human hair comprising the steps of:
a) mixing a base composition containing a water phase comprised of sodium hydroxide in water, and an oil phase, wherein the water phase is dispersed in the oil phase in the form of water in oil emulsion micelles, with an additive composition selected from the group consisting of a water in oil emulsion and an anhydrous oil composition, to yield a hair relaxer composition,
b) applying the hair relaxer composition to the hair for a period of time sufficient to relax the hair,
c) conditioning the hair with a conditioning composition.

The formulations of the base and additive compositions as well as the amounts of each used are set forth herein. The hair is sectioned into quadrants and the relaxer composition is applied by either using a brush, combing, and smoothing or massaging the mixture in with the fingers. The relaxer composition is left on the hair for 5 to 30 minutes, more preferably 8 to 26 minutes. Upon expiration of the desired time period, the hair is washed with a low pH conditioning shampoo which has a pH range of 4.0 to 6.0. The hair is then rinsed clean and dried. The hair relaxer of the invention is more effective in relaxing curly or kinky hair, causes less scalp irritation, and exhibits improved shelf stability over the prior art compositions. Tests were conducted in order to substantiate that the relaxer of the invention was more effective than the prior art relaxers in straightening hair. The test method for ascertaining relaxer effectivenes is as set forth in Example 8. The method of Example 8 is also the subject of patent application Ser. No. 896,525, now U.S. Pat. No. 5,205,300 filed on the same day as this application.

The invention will be further described in connection with the following examples which are set forth for the purposes of illustration only.

EXAMPLE 1

A relaxer base composition in accordance with the invention was made as follows:

|  | w/w % | | |
| --- | --- | --- | --- |
|  | MILD | Regular | Super |
| Stearyl alcohol | 14.00 | 14.00 | 14.00 |
| PEG-75 lanolin | 4.00 | 4.00 | 4.00 |
| Petrolatum | 18.00 | 18.00 | 18.00 |
| Polawax | 5.50 | 5.50 | 5.50 |
| Paraffin | 1.50 | 1.50 | 1.50 |
| Propylene glycol | 5.00 | 5.00 | 5.00 |
| Hydrolyzed animal protein | 5.00 | 5.00 | 5.00 |
| Stearic acid | 1.50 | 1.50 | 1.50 |
| Sodium hydroxide (50%) | 6.00 | 6.50 | 7.00 |
| Water | 39.20 | 38.70 | 38.20 |
| Fragrance | 0.30 | 0.30 | 0.30 |

The base composition was made by combining and heating the oils to 180° F. The water was heated to 180° F. The water was added to the oil phase with stirring.

The propylene glycol was added when the temperature reached 170°-180° F. When the temperature cooled to around 160° F. the hydrolyzed animal protein was added. The sodium hydroxide was added at 110°-120° F., after which the fragrance was added. When the mixture was cooled to 95°-105° F. the product was placed in containers.

EXAMPLE 2

Additive compositions in accordance with the invention was made as follows:

|  | w/w % | |
|---|---|---|
|  | (w/o emulsion) | anhydrous oil |
| Octoxynol-1 | 25.00 | 50.0 |
| Oleyl Alcohol | 9.70 | 19.7 |
| Mineral oil | 30.00 | 30.0 |
| PEG-75 lanolin | 4.00 |  |
| Methylparaben | 0.20 |  |
| Propylparaben | 0.10 |  |
| Butylparaben | 0.10 |  |
| Fragrance | 0.30 | 0.30 |
| Water | 30.6 |  |

The water in oil emulsion additive was made by combining and heating all oils to 180° F. The preservative was also added at this time. The water was separately heated to 180° F. and added to the oil phase. When the mixture was cooled to 120° F. the fragrance was added. When the mixture was cooled to 90° F. it was placed into containers.

The anhydrous additive was made by combining all ingredients and heating the mixture to 120°-140° F. The mixture was stirred until uniformly mixed and cooled to 90° F.

EXAMPLE 3

The relaxer composition of the invention was made by mixing 250 grams of tee base composition of Example 1 and 50 grams of the additive compositon of Example 2 immediately prior to use. The mixture was immediately applied to the hair in the usual fashion, i.e. the hair was sectioned into quadrants and the relaxer compositon applied by working the composition into the hair. The composition was left on the hair for 13-26 minutes depending on the porosity of the hair as determined by a skilled beauty technician according to methods well known to skilled beauty technicians. For example, if hair was porous, the relaxer composition was left on the hair from 13-17 minutes. If the hair was of medium porosity the relaxer composition was left on the hair from 18-22 minutes, and if hair was nonporous the relaxer was left on the hair from 23-26 minutes.

After the appropriate time period, the hair was shampooed with neutralizing shampoo, an acidic formulation having a pH range of 4.0-6.0. The shampoo treatment acted to neutralize the relaxer. The hair was rinsed and towel dried.

EXAMPLE 4

The mild, regular, and super base compositions of Example 1 were compared with a commercial lye based relaxer, and with a commercial no lye calcium hydroxide base formulation. The variables compared were water content, stability at 120° F. and the requirement for milling to achieve the micelle configuration desired in a base composition. The formulations of the commercial lye base composition (LYE), and the commercial calcium hydroxide no lye base compositon (CAOH) were as follows:

|  | w/w % | |
|---|---|---|
|  | LYE | CAOH |
| Petrolatum | 13.50 | 11.31 |
| Polawax | 12.50 | 14.40 |
| Hexylene glycol | 5.50 | 5.80 |
| Hydrolyzed animal protein | 0.20 | — |
| NaOH | 2.12 | — |
| Water | 42.78 | 44.89 |
| Fragrance | 0.40 | 0.30 |
| Mineral oil | 23.00 | 17.40 |
| Ca(OH)$_2$ | — | 5.90 |

The base compositions of Example 1 (hereinafter referred to as "Mild", "Regular", and "Super") were compared with the above "LYE" and "CAOH" formulations as follows:

|  | Mild | Reg. | Super | LYE | CAOH |
|---|---|---|---|---|---|
| Processing (req. milling[1]) | NO | NO | NO | YES | NO |
| Water content (%) |  | 42-45 |  | 43-48 | 45-50 |
| Stability at 120° F. |  | greater than 1 mo. |  | max. 24 h. | long term not est. |

[1]milling is generally required to achieve the micelle configuration in the base compositions. It is a distinct advantage to eliminate the process of milling for it is time intensive. Further, if base compositions require milling to achieve micelles, then when the base composition ages during normal shelf life, the micelles break down and result in product instability. Indeed, in the LYE formulation, if the micelle configuration has deteriorated the product is no longer suitable for use.

The above comparative studies also show that the relaxer base compositions of the invention exhibit much improved stability over the prior art formulations. The Mild, Regular, and Super formulations exhibit stabilities of greater than one month at 120° F. The LYE formulation exhibits a maximum stability of 24 hours at 120° F. Stability at 120° F. was not determined for the CAOH sample.

The above studies also show that the compositions of the invention contain less water than the prior art compositions. This is a particularly unique feature since prior art relaxer compositions generally always required about a 50/50 ratio of water to oil or hydrophilic/lipophilic components in order to remain stable and effective.

EXAMPLE 4

The Mild, Regular and Super base compositions of Example 1 were mixed with the additive of Example 2, and compared with the LYE and CAOH formulations of Example 3. In the LYE formulation no additive is added whereas in the CAOH formulation the additive is a guanidine hydroxide containing mixture of the following formulation which is added immediately prior to use:

|  | w/w % |
|---|---|
| FD&C red #4 | 0.014 |
| Hexylene glycol | 0.500 |
| cellulosic gum | 0.050 |
| guanidine carbonate | 15-25 |
| water | QS100 |

|  | Mild | Reg. | Super | LYE | CAOH |
|---|---|---|---|---|---|
| Mix ratio |  | 250 g. base + 50 g. additive |  | No additive | 201 g. base + 68 g. additive |

| | | | | | |
|---|---|---|---|---|---|
| Ave % NaOH | 1.95 | 2.175 | 2.35 | *** | — |
| Water content (%) | | 40–43 | | 43–48 | 53–57 |
| R.T. stability | greater than 1 mo | | | indef | 24 hr. |

***The mild, regular, and super formulations of the R/R relaxer contained approximately 2.00, 2.125, and 2.25 percent sodium hydroxide respectively.

As is evident from the above, the relaxer composition of the invention contains less water, and in the case of the Super formulation, more sodium hydroxide, and is stable for one month at room temperature even after mixing the base composition with the additive composition. The LYE formulation contained more water and with respect to the Super formulation, less sodium hydroxide and remained stable indefinitely at room temperature. The CAOH formulation contained the most water of all the formulations and generally remained stable after mixing the base compostion and the additive composition, for only 24 hours.

EXAMPLE 5

In order to determine the relationship between the concentration of sodium hydroxide in a relaxer and the level of scalp irritation, the relaxer composition of the invention was tested for scalp irritation by varying the levels of sodium hydroxide in the relaxer composition.

Relaxer compositions of the following NaOH concentrations were prepared as follows:

2.1 percent: 210 grams of the Mild base composition of Example 1 was mixed with 90 grams of the additive composition of Example 2.

2.25 percent: 225 grams of the Mild base composition of Example 1 was mixed with 75 grams of the additive composition of Example 2.

2.4 percent: 240 grams of the Mild base composition of Example 1 was mixed with 60 grams of the additive composition of Example 2.

2.7 percent: 249 grams of the Regular base composition of Example 1 was mixed with 51 grams of the additive composition of Example 2.

3.0 percent: 257 grams of the Super base composition of Example 1 was mixed with 43 grams of the additive composition of Example 2.

The above compositions were applied to the hair of volunteers by sectioning the hair into quadrants and applying the composition by working in with a brush, comb, or the fingers. The relaxer compositions were left on the hair for 8–26 minutes. The volunteers were asked to rate discomfort according to the following scale:

| | |
|---|---|
| 0 - | no discomfort |
| 1 - | tingling |
| 2 - | hot |
| 3 - | sting |
| 4 - | light burning |
| 5 - | burning - remove relaxer |

The results, as set forth in FIG. 3, illustrate that the relaxer compositions of the invention (referred to as Relaxer 2000 in FIG. 3) do not result in any scalp irritation or discomfort up to a concentration of about 2.4 percent sodium hydroxide. After a concentration of 2.4 percent sodium hydroxide is achieved, the amount of scalp discomfort caused by Relaxer 2000 is in direct proportion to the concentration of sodium hydroxide in the composition.

Similar tests were not conducted with LYE relaxer. Since no direct relationship between scalp irritation and water level or scalp irritation vs relaxer penetration into the hair fiber was determined (as set forth in the succeeding examples), it was assumed that the same disparities would exist in varying the levels of NaOH. For that reason, and also to prevent model discomfort, no tests were conducted with LYE relaxer at increased concentrations of NaOH.

EXAMPLE 6

To determine if there was any correlation between the amount of percentage of water in a relaxer formulation and the level of scalp irritation, the LYE formulation of Example 3 was compared with the LYE formulation of Example 3 to which an additional 6 percent of water was added (LYE+6% $H_2O$). The LYE and LYE+6% $H_2O$ formulations were tested on two models by applying the LYE formulation to one half of each head and the LYE+6% $H_2O$ formulation to the other half of each head. The results are as follows:

Model 1: both the LYE side of the head and the LYE+6% $H_2O$ side burned and had to be removed after 10 minutes.

Model 2: no burning on either the LYE side of the head or the LYE+6% $H_2O$ side when both relaxers stayed on for the full 26 minutes.

The results show that the in the LYE relaxer (which was previously identified as the prior art relaxer), there is no correlation between the amount of water in the relaxer and the degree of scalp irritation. This is further illustrated in FIG. 4.

EXAMPLE 7

The correlation between water level and scalp irritation was determined in the relaxer composition of the invention. A first sample was obtained by mixing 250 grams of the Regular base composition of Example 1 with 50 grams of the additive composition of Example 2 (hereinafter referred to as "Relaxer 2000"). A second comparative sample was obtained by mixing 250 grams of the Regular base composition of Example 1 with 50 grams of the additive composition of Example 2, after which an additional 5% $H_2O$ was added to the second sample (hereinafter referred to as "Relaxer 2000+5% $H_2O$"). Both samples were tested on two heads by applying Relaxer 2000 to half a head and Relaxer 2000+5% $H_2O$ to the other half. Both compositions were left on the head for a maximum of 26 minutes. The results were as follows:

Model 1: No irritation on Relaxer 2000 side, tingling on Relaxer 2000+5% $H_2O$ side.

Model 2: No irritation on Relaxer 2000 side, itching on Relaxer 2000+5% $H_2O$ side.

As is illustrated in FIG. 5, there is a direct, positive correlation between scalp irritation and the level of water in the Relaxer 2000 composition.

EXAMPLE 8

Test to Determine Relaxer Effectiveness

A number of subjects were tested by applying the relaxer of the invention (hereinafter "Relaxer 2000") to one half head and the lye based relaxer previously identified as LYE in Example 3 to the other half head. The relaxer effectiveness was determined with the following novel procedure which is disclosed and claimed in co-pending application Case Docket Rev 92-8 entitled "Method for Testing Hair Relaxer Effectiveness", which application is filed on the same day as this application and which is hereby incorporated by reference:

1. Before applying relaxer, representative samples of hair from both the right and left side of the model's head were obtained by snipping a small portion of hair at the scalp that looked representative of the hair sample in general.
2. One end of the sample was placed in a clamp or other device to secure it. The other end of the sample was grasped in a hemostat and pulled gently til straight between the clamp and the hemostat. A 0.5 inch section of hair was cut, ensuring that the small amount of hair clamped within the hemostat was included within this 0.5 inch measurement.
3. The hair clipping was released and allowed to fall onto white paper. The length of the clipping was then measured and recorded.
4. This hair clipping was then wet by placing into a petri dish containing water. The length of the clipping was measured within 10-15 seconds while in the water. The measurement was recorded.
5. The beautician then determined whether the model's hair was porous, nonporous, or of medium porosity. One half of each model's head was treated with Relaxer 2000 which comprised a mixture of 250 grams of the Regular base composition of Example 1 and 50 grams of the additive composition of Example 2. The other half of the model's head was treated with Revlon-Realistic lye based relaxer of Example 3. The relaxer compositions were left on the head for 13-26 minutes, depending on the porosity of the model's hair. For example, the relaxer was left on the head from 13-17 minutes if the model's hair was porous, 18-22 minutes if the hair was of medium porosity, and 23-26 minutes if the hair was nonporous.
6. After expiration of the appropriate time period, each model's hair was washed with Herbal Deep Clean, a low pH conditioning shampoo having a pH of 4.0-6.0.
7. Test samples were again taken on the left and right sides of the head in accordance with (1) and (2) above. The length of each clipping was measured dry and then wet in accordance with (3) above. The percentage of full relaxation was calculated for both wet and dry samples as follows:

$$\% \text{ full relaxation} = \frac{(\text{length of hair after relaxation}) - (\text{length of hair before relaxation})}{(\text{length of hair sample cut})}$$

The % relaxation for both wet and dry samples was calculated. The results are as set forth below:

| Hair length measurements before relaxation on dry hair | | Hair length measurements after relaxation on dry hair | |
|---|---|---|---|
| 2000 | LYE | 2000 | LYE |
| 0.399 | 0.373 | 0.500 | 0.500 |
| 0.383 | 0.442 | 0.428 | 0.420 |
| 0.289 | 0.270 | 0.488 | 0.500 |
| 0.158 | 0.196 | 0.487 | 0.314 |
| 0.265 | 0.295 | 0.355 | 0.207 |
| 0.398 | 0.372 | 0.500 | 0.500 |
| 0.320 | 0.365 | 0.488 | 0.482 |
| 0.407 | 0.370 | 0.480 | 0.437 |
| 0.362 | 0.395 | 0.410 | 0.399 |
| 0.407 | 0.405 | 0.486 | 0.471 |
| 0.377 | 0.358 | 0.500 | 0.435 |

-continued

| Hair length measurements before relaxation on dry hair | | Hair length measurements after relaxation on dry hair | | |
|---|---|---|---|---|
| 2000 | LYE | 2000 | LYE | |
| 0.179 | 0.241 | 0.357 | 0.322 | |
| 0.390 | 0.359 | 0.402 | 0.327 | |
| Average Length in Inches | | | | |
| 0.333 | 0.338 | 0.452 | 0.409 | |
| 0.083 | 0.073 | 0.053 | 0.088 | SD |
| 0.285 | 0.294 | 0.420 | 0.356 | |
| to | to | to | to | 95% |
| 0.383 | 0.382 | 0.484 | 0.462 | |
| % Relaxation based on 95% confidence level | | | | |
| 57 | 59 | 84 | 71 | |
| to | to | to | to | |
| 77 | 76 | 97 | 92 | |

| Hair length measurements before relaxation on wet hair | | Hair length measurements after relaxation on wet hair | | |
|---|---|---|---|---|
| 2000 | LYE | 2000 | LYE | |
| 0.353 | 0.296 | 0.500 | 0.496 | |
| 0.316 | 0.398 | 0.428 | 0.420 | |
| 0.200 | 0.196 | 0.468 | 0.500 | |
| 0.148 | 0.174 | 0.487 | 0.282 | |
| 0.321 | 0.277 | 0.313 | 0.196 | |
| 0.369 | 0.354 | 0.490 | 0.487 | |
| 0.276 | 0.334 | 0.415 | 0.455 | |
| 0.359 | 0.370 | 0.462 | 0.432 | |
| 0.316 | 0.378 | 0.395 | 0.359 | |
| 0.380 | 0.373 | 0.481 | 0.464 | |
| 0.352 | 0.318 | 0.492 | 0.429 | |
| 0.169 | 0.234 | 0.305 | 0.312 | |
| 0.360 | 0.295 | 0.402 | 0.300 | |
| Average Length in Inches | | | | |
| 0.301 | 0.307 | 0.434 | 0.395 | |
| 0.076 | 0.069 | 0.063 | 0.092 | SD |
| 0.255 | 0.265 | 0.395 | 0.359 | |
| to | to | to | to | 95 |
| 0.347 | 0.349 | 0.471 | 0.451 | |
| % Relaxation based on 95% confidence level | | | | |
| 51 | 53 | 79 | 68 | |
| to | to | to | to | |
| 69 | 70 | 94 | 90 | |

SD means Standard Deviation
95% means 95% confidence level

The above data illustrates that the relaxer of the invention was more effective in achieving relaxation than the commercial lye based formula.

8. The beautician also rated the hair of fifty six models after relaxation in accordance with the following scale:

```
8 = no evidence of curl
7 = minimal evidence of curl
6 = straightening but with some evidence of curl
5 = slight straightening - alot of curl
4 = poor - no straightening.
```

8. The results of the rating were as follows:

| | Rating given | | | | | |
|---|---|---|---|---|---|---|
| | Relaxer 2000--- | | | R/R | | |
| | 8 | 7 | 6 | 8 | 7 | 6 |
| No. Women | 52 | 3 | 1 | 41 | 12 | 3 |

None of the ratings assessed were less than 6 so rating numbers 4 and 5 are not included in the above table.

These results show that Relaxer 2000 was more effective in relaxing hair.

EXAMPLE 9

The models whose hair was relaxed in Example 8 were asked to return to the salon two to three weeks after the initial procedure in order to determine the degree to which hair reverted to its natural curly state after two to three weeks. The following test method for determining curl reversion was employed. This method is also disclosed and claim in copending application Case Docket Rev 92-8 entitled "Method for Determining the Effectiveness of Hair Relaxer Treatment", filed on the same day as this application, and which is hereby incorporated by reference.

1. Test samples of dry hair were obtained from the right and left side of each model's head by snipping representative samples beginning at the scalp.
2. Hair regrowth of ¼ inch was assumed in the two to three week period so ¼ inch of the hair sample taken from nearest the scalp was snipped off.
3. A 0.5 inch section of hair was cut by clamping on end of the hair sample in a clamp or other securing device. The other end of the sample was grasped in a hemostat and pulled gently til straight. A 0.5 inch section was cut.
4. The length of the hair was measured in its natural state and the percent of full relaxation calculated in accordance with the formula of (7) in Example 8.
5. The measuring process was repeated with wet hair and the percent of full relaxation calculated again.
6. The % relaxation figure from Example 8 was compared with the % relaxation for the same model 2-3 weeks after treatment.

| Hair length measurements after relaxation on dry hair | | Hair length measurements 2-3 wks later on dry hair | | | |
|---|---|---|---|---|---|
| 2000 | LYE | 2000 | LYE | | |
| 0.500 | 0.500 | 0.500 | 0.500 | | |
| 0.488 | 0.500 | 0.494 | 0.490 | | |
| 0.487 | 0.314 | 0.500 | 0.492 | | |
| 0.355 | 0.207 | 0.466 | 0.470 | | |
| 0.488 | 0.482 | 0.495 | 0.476 | | |
| 0.410 | 0.399 | 0.395 | 0.471 | | |
| 0.486 | 0.471 | 0.500 | 0.490 | | |
| 0.500 | 0.435 | 0.500 | 0.497 | | |
| 0.357 | 0.322 | 0.462 | 0.389 | | |
| Average Length in Inches | | | | | |
| 0.457 | 0.413 | 0.481 | 0.454 | | |
| 0.056 | 0.096 | 0.032 | 0.071 | SD | |
| 0.417 | 0.344 | 0.458 | 0.403 | | 95% |
| to | to | to | to | | |
| 0.497 | 0.482 | 0.504 | 0.505 | | |
| % Relaxation based on 95% confidence level | | | | | |
| 83 | 69 | 92 | 80 | | |
| to | to | to | to | | |
| 99 | 96 | 101 | 101 | | |

| Hair length measurements after relaxation on wet hair | | Hair length measurements 2-3 wks later on wet hair | | | |
|---|---|---|---|---|---|
| 2000 | LYE | 2000 | LYE | | |
| 0.500 | 0.496 | 0.500 | 0.500 | | |
| 0.468 | 0.500 | 0.475 | 0.476 | | |
| 0.487 | 0.282 | 0.498 | 0.489 | | |
| 0.313 | 0.196 | 0.442 | 0.458 | | |
| 0.490 | 0.487 | 0.485 | 0.236 | | |
| 0.415 | 0.455 | 0.486 | 0.476 | | |
| 0.395 | 0.359 | 0.388 | 0.456 | | |
| 0.481 | 0.464 | 0.500 | 0.494 | | |
| 0.305 | 0.312 | 0.418 | 0.389 | | |
| Average Length in Inches | | | | | |
| 0.435 | 0.398 | 0.469 | 0.446 | | |
| 0.071 | 0.099 | 0.037 | 0.076 | SD | |
| 0.384 | 0.327 | 0.443 | 0.392 | | |
| to | to | to | to | | 95% |
| 0.486 | 0.496 | 0.495 | 0.500 | | |
| % Relaxation based on 95% confidence level | | | | | |
| 77 | 65 | 89 | 78 | | |
| to | to | to | to | | |
| 97 | 99 | 99 | 100 | | |

The above results demonstrate the relaxer of the invention exhibits a slightly better resistance to curl reversion.

While the invention has been described in connection with the preferred embodiment, it is not intended to limit the scope of the invention to the particular form set forth, but, on the contrary, it is intended to cover such alternatives, modifications, and equivalents as may be included within the spirit and scope of the amended claims.

What is claimed is:

1. A method for manufacturing a relaxer for human hair comprising combining the following components (a) and (b) immediately prior to use:
   a) 40-90 parts of a base composition comprising 35-50% by weight of the base composition of an oil phase, 1-20% by weight of the base composition of a surfactant selected from the group consisting of Octyoxynol 1-70, stearic acid, Polysorbate 20-100, PEG 2-150 stearate, Steareth 2-100, Laneth 5-75, PEG 1-100 lanolin, or mixtures thereof, and 35-50% by weight of the base composition of a water phase containing 40-60% by weight of the water phase of sodium hydroxide;
   b) 10-60 parts of an oil in water additive composition consisting essentially of, by weight of the additive composition, 0.1-70% water, 30-90% of an oil selected from the group consisting of oleyl alcohol, mineral oil, PEG-75 lanolin, or mixtures thereof, and 0.01-35% of a surfactant which is an octylphenoxyethanol of the formula

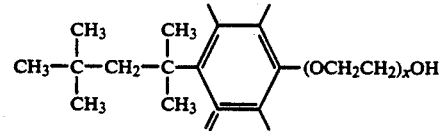

wherein x is 1-50,
to yield a finished relaxer composition comprising 35-45% water, 55-60% oil, and 0.01-35% sodium hydroxide.

2. The method of claim 1 wherein the surfactant of component (a) is Octoxynol-1.

3. The method of claim 2 wherein the additive composition additionally contains an ingredient selected from the group consisting of preservative, fragrance, and mixtures thereof.

4. A method for relaxing human hair comprising combining the following components (a) and (b) immediately prior to use:

a) 40-90 parts of a base composition comprising 35-50% by weight of the base composition of an oil phase, 1-20% by weight of the base composition of a surfactant selected from the group consisting of Octyoxynol 1-70, stearic acid, Polysorbate 20-100, PEG 2-150 stearate, Steareth 2-100, Laneth 5-75, PEG 1-100 lanolin, or mixtures thereof, and 35-50% by weight of the base composition of a water phase containing 40-60% by weight of the water phase of sodium hydroxide; with b) 10-60 parts of an oil in water additive composition consisting essentially of, by weight of the additive composition, 0.1-70% water, 30-90% of an oil selected from the group consisting of oleyl alcohol, mineral oil, PEG-75 lanolin, or mixtures thereof, and 0.01-35% of a surfactant which is an octylphenoxyethanol of the formula

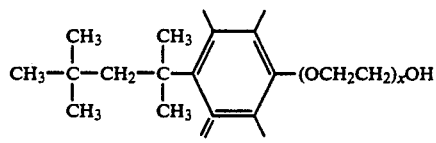

wherein x is 1-50;

to yield a finished relaxer composition comprising 35-45% water, 55-65% oil, and 1.5-3.5% sodium hydroxide, c) applying the mixture of (a) and (b) to the hair for a period of time sufficient to relax the hair; and (d) washing the hair with a low pH conditioning shampoo having a pH of 3.5 to 6.0.

5. The method of claim 4 wherein the mixture of (a) and (b) is applied to the hair for 5-30 minutes.

6. The method of claim 5 wherein the low pH conditioning shampoo has a pH of 4.0-6.0.

* * * * *